United States Patent
Bombardelli

(10) Patent No.: US 8,206,759 B2
(45) Date of Patent: Jun. 26, 2012

(54) METHOD OF REDUCING BLOOD CHOLESTEROL AND TRIGLYCERIDE LEVELS USING COMBINATIONS OF VASOPROTECTIVE AGENT

(75) Inventor: Ezio Bombardelli, Gropello Cairoli (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 13/033,826

(22) Filed: Feb. 24, 2011

(65) Prior Publication Data

US 2011/0142967 A1 Jun. 16, 2011

Related U.S. Application Data

(62) Division of application No. 12/721,015, filed on Mar. 10, 2010, now abandoned, which is a division of application No. 10/562,214, filed as application No. PCT/EP2004/006507 on Jun. 17, 2004, now abandoned.

(30) Foreign Application Priority Data

Jun. 27, 2003 (IT) .................................. MI03A1313

(51) Int. Cl.
*A01N 65/00* (2009.01)

(52) U.S. Cl. ....................................................... 424/725

(58) Field of Classification Search ........................ None
See application file for complete search history.

(56) References Cited

U.S. PATENT DOCUMENTS

| | | | |
|---|---|---|---|
| 5,846,569 A | 12/1998 | Anderson et al. | |
| 6,419,962 B1 | 7/2002 | Yokoyama et al. | |
| 6,667,064 B2 | 12/2003 | Surette | |
| 6,733,799 B2 | 5/2004 | Cheruvanky et al. | |
| 2001/0014669 A1 | 8/2001 | Bok et al. | |

FOREIGN PATENT DOCUMENTS

| | | |
|---|---|---|
| EP | 0 659 402 | 6/1995 |
| EP | 0 818 225 | 1/1998 |
| KR | 2001009590 | 2/2001 |
| WO | WO 98/33494 | 8/1998 |
| WO | WO 99/48386 | 9/1999 |
| WO | WO 00/66078 | 11/2000 |

OTHER PUBLICATIONS

Pons P et al: "Effects of Successive Dose Increases of Policosanol on the Lipid Profile of Patients With Type Ii Hypercholesterolaemia and Tolerability to Treatment", International Journal of Clinical Pharmacology Research, Bioscience Ediprint, Geneva,,, CH, vol. 14, No. 1, 1994, pp. 27-33, XP00095179, ISSN: 0251-1649, cited in the application, p. 27, 1paragraphs 1,2.
Scient Direct, 13 pages, 2006.
Forever looking younger, 6 pages, 2009.
A carrot a day, 2 pages, 2008.
Policosanol, 4 pages, 2009.
AAFP, 11 pages, 2004.
Dr. Betty Kamen, 9 pages, 1999.
Rice Bran oil info, 3 pages, 2009.
Silverkey member, 3 pages, 2008.
Cravatto et al., 2 pages, 2009.
Practice Clinical Vistas, 2002, 1 page.

*Primary Examiner* — Michael Meller
(74) *Attorney, Agent, or Firm* — Young & Thompson

(57) ABSTRACT

Combinations of vasoprotective agents useful for the treatment of reducing blood cholesterol and triglyceride levels induced by an excess of plasma lipids. The agents include polycosanols, tocotriends and/or lycopene, procyanidole oligomers and vegetable oil rich in insaturated fatty acids.

5 Claims, No Drawings

METHOD OF REDUCING BLOOD CHOLESTEROL AND TRIGLYCERIDE LEVELS USING COMBINATIONS OF VASOPROTECTIVE AGENT

CROSS REFERENCE TO RELATED APPLICATIONS

This application is a division of co-pending application Ser. No. 12/721,015 filed on Mar. 10, 2010, which is a division of application Ser. No. 10/562,214 filed on Dec. 23, 2005, which is the 35 U.S.C. §371 national stage of International PCT/EP2004/006507 filed on Jun. 17, 2004, which claims priority to Italian Application No. MI2003A001313 filed on Jun. 27, 2003. The entire contents of each of the above-identified applications are hereby incorporated by reference.

FIELD OF THE INVENTION

The present invention relates to combinations of vasoprotective agents useful for the prevention and the treatment of vascular injuries induced by an excess of plasma lipids.

The combinations of the invention reduce blood cholesterol and triglyceride levels while protecting the vascular wall against the injuries induced by overproduction of free radicals and cholesterol oxidized forms, thus strengthening the wall.

DISCLOSURE OF THE INVENTION

The present invention relates to combinations of vasoprotective agents and compositions comprising said combinations.

The arteriosclerotic disease is a very complex phenomenon not only connected with lipid conditions, therefore any synergetic actions concerning vascular protection and reduction of free radicals overproduction have large therapeutic interest. Chronic degenerative diseases such as cardiovascular diseases do not have a single origin. High trigyceride and cholesterol levels, accompanied by altered ratios of the lipoprotein fractions, as well as hypertension, undoubtedly induce marked vascular injuries with unfavourable prognosis. There is therefore the need to decrease blood cholesterol and trigycerides levels, while strengthening and protecting the arterial walls.

It has now been found that this objective can advantageously be attained by combining vasoprotective agents having different mechanisms of action. The invention relates in particular to pharmaceutical, dietetic or nutritional compositions comprising:
  one or more polycosanols or esters thereof, either pure or as extracts;
  ocotrienol and/or lycopene, preferably tocotrienol;
  one or more procyanidole oligomers optionally complexed with phospholipids;
  a vegetable oil rich in ω-3, ω-6 unsaturated fatty acids.

The hypocholesterolemizing, or more generally anti-atherosclerotic, activity of each single component of the combination is known, but only through the combined use thereof particularly remarkable preventive or therapeutic effects can be attained.

The use and the preparation of procyanidole oligomers complexed with phospholipids as anti-atherosclerotic agents are disclosed in WO 99/29331.

Polycosanols, as well as ω-3, ω-6 unsaturated fatty acids, have been the object of investigations in the cardiologic and cardio-vascular fields for some time (*Int J Clin Pharm Res* 1994; 14:27-33 and *Ann. Intern. Med.* 1999; 130:554-62, respectively) while tocotrienol and lycopene, belonging to the family of carotenoids, have been extensively studied as agents able to prevent lipoperoxidation and formation of free radicals, and also as chemo-preventive agents (*Clin. Biochem* 1999; 32:309-19).

The polycosanols used according to the invention are straight, long chain aliphatic alcohols, typically straight alcohols having 24 to 30 carbon atoms, obtainable by saponification of waxes from vegetable materials such as olive, wheat, rice, sugar cane and other sources. These compounds can be used either in the free form or esterified with ferulic acid or other cinnamates variously substituted at the phenyl moiety, such as $p\text{-}NO_2$, $p$-OH, and $m$-Cl cinnamates.

The procyanidole oligomers for use according to the invention can be obtained from *Vitis vinifera*, *Camellia sinensis*, *Aesculus hippocastanum*, *Olea europea*.

The vegetable oil is preferably selected from *Enothera biennis*, *Ribes nigrum* or *Portulaca oleracea* oils, more preferably *Enothera biennis* oil. The ω-3, ω-6 unsaturated fatty acids present in said oils can optionally be transformed into the corresponding alkyl esters, in particular the corresponding ethyl esters, by transesterification, for example by treating the oil with ethanol and $H_2SO_4$ in the presence of benzene to azeotropically remove water.

The compositions of the invention can further contain luteolin per se or in the form of 7,3',4'-hydroxyethyl derivatives.

The formulations of the invention can contain 5 to 30 mg, preferably 15 mg, of polycosanols; 1 to 50 mg, preferably 8 mg, of tocotrienol or lycopene; 30 to 200 mg of proanthocyanidins or 100 to 320 mg of proanthocyanidins complexed with phospholipids, and 150 to 300 mg of vegetable oils, per unit dosage form.

20 Patients suffering from essential hyperlipidemia with carotid plaques were treated with a formulation of the invention having the following composition:

| | | |
|---|---|---|
| Rice polycosanols (70% polycosanols) | | 15 mg |
| Tocotrienol | | 14 mg |
| Procyanidole oligomers/phospholipids | | 320 mg |
| *Enothera biennis* oil | q.s. to | 500 mg |

After two month treatment with two capsules/day, patients showed normalized lipid parameters and improved conditions of the plaques, as evidenced by EcoDoppler.

The following examples illustrate the invention in greater detail:

EXAMPLE I

| | | |
|---|---|---|
| Polycosanols from rice or olive residues oils | | 15 mg |
| Tocotrienol | | 14 mg |
| Procyanidole oligomers/phospholipids | | 320 mg |
| *Enothera biennis* oil | q.s. to | 500 mg |

EXAMPLE II

| | | |
|---|---|---|
| Polycosanols from olive residues oil esterified with ferulic acid | | 30 mg |
| Tocotrienol | | 14 mg |
| Procyanidole oligomers/phospholipids | | 250 mg |
| Enothera biennis oil | q.s. to | 500 mg |

EXAMPLE III

| | | |
|---|---|---|
| Octacosanyl ferulate | | 12 mg |
| Tocotrienol | | 12 mg |
| Epigallocatechin gallate/phosphatidyl choline 1:1 | | 250 mg |
| Ethyl eicosapentanoate | q.s. to | 500 mg |

EXAMPLE IV

| | | |
|---|---|---|
| Polycosanols from rice or olive residues oils esterified with ferulic acid | | 15 mg |
| Tocotrienol | | 14 mg |
| Procyanidole oligomers/phospholipids | | 250 mg |
| Enothera biennis oil | q.s. to | 500 mg |

EXAMPLE V

| | | |
|---|---|---|
| Polycosanols from rice or olive residues oils | | 15 mg |
| Tocotrienol | | 14 mg |
| Procyanidole oligomers | | 150 mg |
| Enothera biennis oil | q.s. to | 500 mg |

What is claimed is:

1. A method for reducing blood cholesterol and triglyceride levels, consisting essentially of administering to a subject in need thereof a combination of a therapeutically effective amount of:
   rice polycosanols;
   at least one of tocotrienol and lycopene;
      proanthocyanidins complexed with phospholipids; and
      a vegetable oil selected from the group consisting of Enothera biennis, Ribes nigrum and Portulaca oleracea oil, wherein the composition is a pharmaceutical, dietetic or nutritional composition.

2. The method as claimed in claim 1, wherein the vegetable oil is Enothera biennis oil.

3. A method for reducing blood cholesterol and triglyceride levels, consisting essentially of administering to a subject in need thereof a combination of a therapeutically effective amount of:
   rice polycosanols;
   at least one of tocotrienol and lycopene;
   proanthocyanidins complexed with phospholipids;
   luteolin; and
   a vegetable oil selected from the group consisting of Enothera biennis, Ribes nigrum and Portulaca oleracea oil, wherein the composition is a pharmaceutical, dietetic or nutritional composition.

4. The method as claimed in claim 1, wherein the therapeutically effect amount is 5 to 30 mg of rice polycosanols, 1 to 50 mg of tocotrienol or lycopene, 100 to 320 mg of proanthocyanidins complexed with phospholipids, and 150 to 300 mg of said vegetable oil, per unitary dosage form.

5. The method as claimed in claim 1, wherein tocotrienol is administered.

* * * * *